United States Patent [19]

Hoffman et al.

[11] Patent Number: 4,916,162
[45] Date of Patent: Apr. 10, 1990

[54] ANTIHYPERCHOLESTEROLEMIC COMPOUNDS

[75] Inventors: William F. Hoffman, Lansdale; Clarence S. Rooney, Worcester; Ta Jyh Lee, Lansdale, all of Pa.

[73] Assignee: Merck & Co., Inc., Rahway, N.J.

[21] Appl. No.: 220,848

[22] Filed: Jul. 18, 1988

Related U.S. Application Data

[63] Continuation of Ser. No. 859,535, May 5, 1986, Pat. No. 4,771,071.

[51] Int. Cl.[4] ............................................. A61K 31/19
[52] U.S. Cl. .................................... 514/574; 560/119;
562/501; 548/272; 548/517; 546/248; 546/207;
544/59; 544/60; 544/149; 544/162; 544/374;
544/403; 514/227.5; 514/227.8; 514/231.5;
514/237.8; 514/238.8; 514/331; 514/326;
514/315; 514/255; 514/529; 514/561; 514/824
[58] Field of Search ................ 560/119; 574/824, 574,
574/561, 529; 562/501

[56] References Cited

U.S. PATENT DOCUMENTS 4,444,784  4/1984  Hoffman et al. .................... 560/119
4,668,699  5/1987  Hoffman et al. .................... 560/119

Primary Examiner—Glennon H. Hollrah
Attorney, Agent, or Firm—Melvin Winokur; Joseph F. DiPrima

[57] ABSTRACT

Novel 3-hydroxy-3-methylglutary-coenzyme A (HMG-CoA) reductase inhibitors which are useful as antihypercholesterolemic agents and are represented by the following general structural formulae (I) and (II):

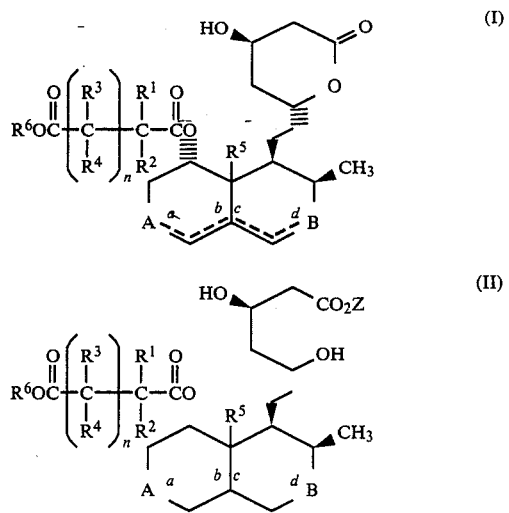

and pharmaceutically acceptable salts of the compounds (II) in which Z is hydrogen are disclosed.

13 Claims, No Drawings

ANTIHYPERCHOLESTEROLEMIC COMPOUNDS

This is a division of application Ser. No. 859,535 filed May 5, 1986; now U.S. Pat. No. 4,771,071.

BACKGROUND OF THE INVENTION

Hypercholesterolemia is known to be one of the prime risk factors for ischemic cardiovascular disease such as arteriosclerosis. To date, there is still no effective antihypercholesterolemic agent commercially available that has found wide patient acceptance. The bile acid sequestrants seem to be moderately effective but they must be consumed in large quantities, i.e. several grams at a time and they are not very palatable.

There are agents known, however, that are very active antihypercholesterolemic agents that function by limiting cholesterol biosynthesis by inhibiting the enzyme, HMG-CoA reductase. These agents include the natural fermentation products compactin and mevinolin and a variety of semi-synthetic and totally synthetic analogs thereof. The naturally occuring compounds and their semi-synthetic analogs have the following general structural formulae:

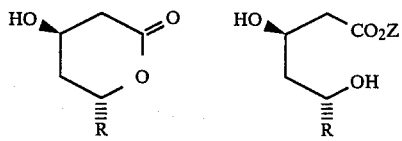

wherein: Z is hydrogen, $C_{1-5}$ alkyl or $C_{1-5}$ alkyl substituted with a member of the group consisting of phenyl, dimethylamino, or acetylamino;

R is :

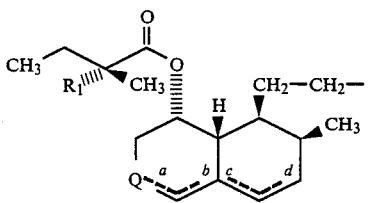

Wherein Q is

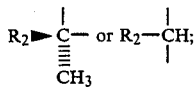

$R_2$ is H or OH:

$R_1$ is hydrogen or methyl; and a, b, c, and d represent optional double bonds, especially where b and d represent double bonds or a, b, c, and d are all single bonds.

U.S. Pat. No. 4,517,373 disclosed semi-synthetic compounds represented by the above general formula wherein R is

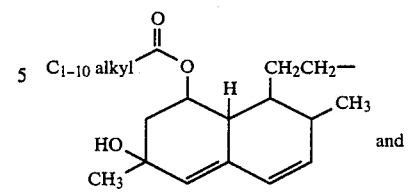

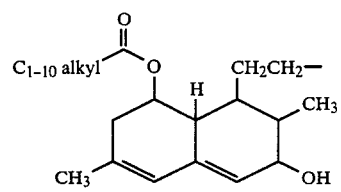

U.S. Pat. No. 4,346,227 and U.S. Pat. No. 4,448,979 also disclose semi-synthetic compounds represented by the above general formula wherein R is

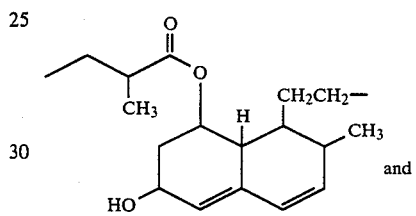

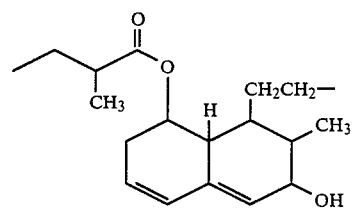

Japanese unexamined patent application J59-122,483-A discloses a semi-synthetic compound represented by the above general formula wherein R is

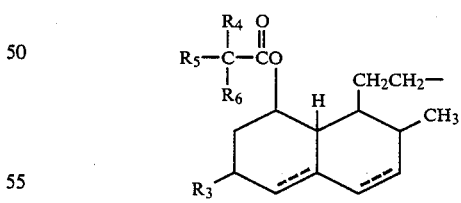

in which $R_3$ is hydrogen or methyl; $R_4$ is hydrogen, halogen or haloalkyl; $R_5$ is hydrogen, halogen or lower alkyl and $R_6$ is halogen, $N_3$, hydroxy, thio, amino, loweralkoxy, lower alkylthio and aralkylthio.

U.S. Pat. No. 4,444,784 discloses 8'-acyloxy derivatives of compactin, mevinolin and the dihydro and tetrahydro anaglogs thereof. Generically disclosed are the compounds represented by the above general formula wherein R is:

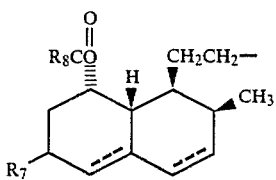

in which $R_7$ is hydrogen or methyl and $R_8$ is $C_{1-10}$ alkyl, $C_{1-10}$ $CF_3$ substituted alkyl, phenyl-$C_{1-3}$ alkyl or substituted phenyl-$C_{1-3}$ alkyl in which the substituent is halo, $C_{1-3}$ alkyl or $C_{1-3}$ alkoxy.

SUMMARY OF THE INVENTION

This invention relates to novel compounds which are HMG-CoA reductase inhibitors and are useful as antihypercholesterolemic agents. Specifically the compounds of this invention are semi-synthetic analogs of compactin, mevinolin, hydroxylated compactin and hydroxylated mevinolin, and the dihydro and tetrahydro analogs thereof which possess a specifically substituted 8'-ester acyl moiety. Additionally, pharmaceutical compositions of these novel compounds, as the sole therapeutically active ingredient, and in combination with bile acid sequestrants are disclosed.

DETAILED DESCRIPTION OF THE INVENTION

The specific HMG-CoA reductase inhibitors of this invention are the compounds represented by the following general structural formulae (I) and (II):

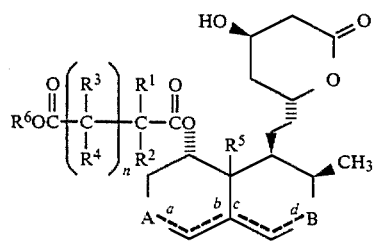
(I)

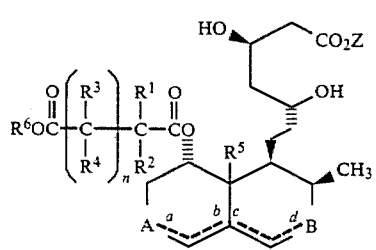
(II)

wherein:

n is 0 to 5;

$R^1$ is $C_{1-3}$ alkyl;

$R^2$ is hydrogen or $C_{1-3}$ alkyl;

$R^3$ and $R^4$ independently are hydrogen $C_{1-3}$ alkyl, $C_{3-7}$ cycloalkyl, phenyl or substituted phenyl in which the substituents are X and Y and when n is 2 to 5, each of the $R^3$s and $R^4$s are independently hydrogen, $C_{1-3}$ alkyl, $C_{3-7}$ cycloalkyl or only one of the $R^3$s and $R^4$s are phenyl or substituted phenyl;

$R^5$ is hydrogen or hydroxy;

$R^6$ is hydrogen or $C_{1-3}$ alkyl:

A is

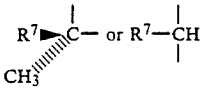

in which $R^7$ is hydrogen or hydroxy;

B is

which $R^8$ is hydrogen or hydroxy; and a, b, c and d represent single bonds, one of a, b, c or d represents a double bond, or both a and c or both b and d represent double bonds provided that when a is a double bond, A is

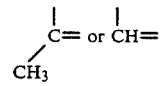

and when d is a double bond, B is

and

X and Y independently are hydrogen, halogen, trifluoromethyl, $C_{1-3}$ alkyl, nitro, cyano or a group selected from:

(a) $R^9O(CH_2)_m$ in which m is 0 to 3 and $R^9$ is hydrogen, $C_{1-3}$ alkyl or hydroxy-$C_{1-3}$ alkyl;

(b)

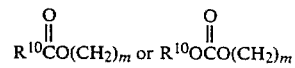

in which $R^{10}$ is hydrogen, alkyl, hydroxy-$C_{2-3}$ alkyl, phenyl, naphthyl, amino-$C_{1-3}$ alkyl, $C_{1-3}$ alkylamino-$C_{1-3}$ alkyl, di($C_{1-3}$ alkyl)amino-$C_{1-3}$ alkyl, hydroxy-$C_{2-3}$ alkylamino-$C_{1-3}$ alkyl or di(hydroxy-$C_{2-3}$ alkyl)amino-$C_{1-3}$ alkyl;

(c)

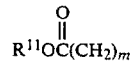

in which $R^{11}$ is hydrogen, $C_{1-3}$ alkyl, hydroxy-$C_{1-3}$ alkyl, $C_{1-3}$ alkoxy-$C_{1-3}$ alkyl, phenyl or naphthyl;

(d)

in which $R^{12}$ and $R^{13}$ independently are hydrogen, $C_{1-3}$ alkyl, hydroxy-$C_{2-3}$ alkyl or together with nitrogen atom to which they are attached form a heterocycle group selected from piperidinyl, pyrrolidinyl, piperaziinyl, morpholinyl or thiomorpholinyl;

(e) $R^{14}S(O)_p(CH_2)_m$ in which p is 0 to 2 and $R^{14}$ is hydrogen, $C_{1-3}$ alkyl, amino, $C_{1-3}$ alkylamino or di($C_{1-3}$ alkyl)amino;

Z is hydrogen, $C_{1-5}$ alkyl or $C_{1-5}$ alkyl substituted with a member of the group consisting of phenyl, dimethylamino or acetylamino;

and pharmaceutically acceptable salts of the compounds of the formula (II) in which Z is hydrogen.

Illustrative of one embodiment of this invention are the compounds of the formulae (I) and (II) wherein $R^5$ is hydrogen, $R^7$ is hydrogen, $R^8$ is hydrogen and a, b, c and represent single bonds or both b and d represent double bonds. Specific compounds are those particular compounds wherein $R^1$ is methyl, $R^2$ is methyl, and $R^3$ and $R^4$ are hydrogen. Exemplifying this embodiment are the following compounds:

(1) 6(R)-[2-[(S)-(2,2-dimethyl-3-methoxy-3-oxopropionyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one;

(2) 6(R)-[2-[8(S)-(2,2-dimethyl-3-methoxycarbonypropionyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one; and their corresponding free hydroxy acids.

Another embodiment of this invention is the class of compounds of the formula (II) wherein Z is hydrogen or $C_{1-5}$ alkyl and pharmaceutically acceptable salts of the compounds of the fromula (II) wherein Z is hydrogen.

The pharmaceutically acceptable salts of this invention include those formed from cations such as sodium, potassium, aluminum, calcium, lithium, magnesium, zinc, and from bases such as ammonia, ethylenediamine, N-methylglucamine, lysine, arginine, ornithine, choline, N,N'-dibenzylethylenediamine, chloroprocaine, diethanolamine, procaine, N-benzylphenthylamine, diethylamine, piperazine, tris(hydroxymethyl)aminomethane, and tetramethylammonium hydroxide.

The compounds of formula (I) are conveniently prepared from compactin, mevinolin, or the appropriate dihydro or tetrahydro analog thereof via the following general synthetic pathway:

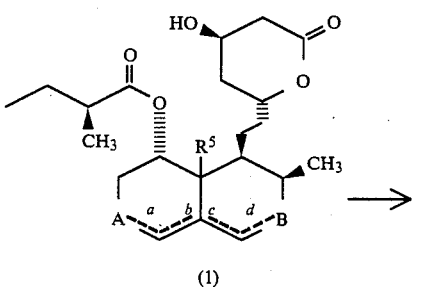

(1)

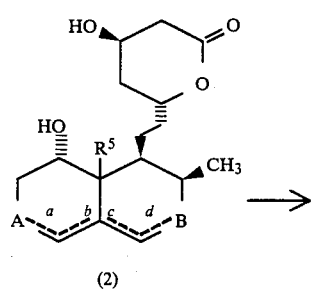

(2)

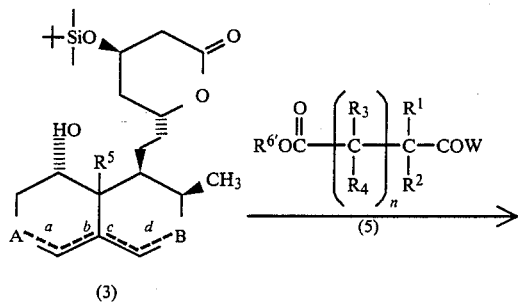

(3)

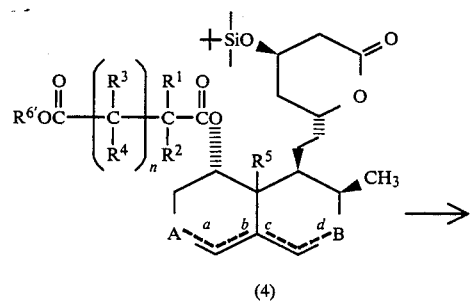

(4)

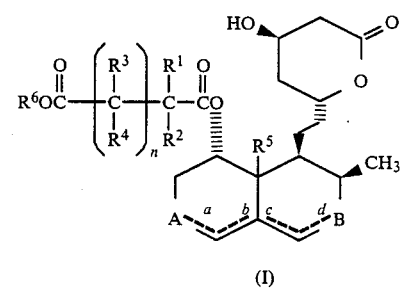

(I)

The starting materials compactin, mevinolin, and their dihydro and tetrahydro analogs are readily available or may be prepared according to fermentation procedures disclosed in U.S. Pat. No. 3,983,140, U.S. Pat. No. 4,049,495, U.S. Pat. No. 4,231,938, U.S. Pat. No. 4,294,846, and U.S. Pat. No. 4,343,814, and the hydrogention procedures disclosed in U.S. Pat. No. 4,351,844. The appropriate starting material of formula (1) is then hydrolyzed under the conditions disclosed in U.S. Pat. No. 4,444,784 to afford the compounds of formula (2). The 4-hydroxy function in the lactone moiety of the compounds of formula (2) is protected with a suitable protecting agent, exemplified here as a dimethyl-t-butysilyl group, according to the procedure disclosed in U.S. Pat. No. 4,444,784. Acylation of the 8'-hydroxy group of the compounds of the formula (3) is accomplished under suitable conditions utilizing the appropriately substituted acids or acid halides of the formula (5) wherein n, $R^1$, $R^2$, $R^3$, and $R^4$ are as described above, except that when $R^6$ contains a hydroxyl group that group is protected with a suitable protecting group such as a trialkylsilyl group and W is hydroxyl or halogen. The protecting groups of the compound of the formula (4) are removed utilizing suitable conditions to afford the compounds of the formula (I). For the compounds of this invention wherein the polyhydronaphthyl moiety is substituted with a hydroxy group, the compound of the Formula (4) is subject to a microbiological hydroxylation after the removal of the protecting groups utilizing the general procedures disclosed in U.S. Pat. No. 4,346,227, U.S. Pat. No. 4,448,979, U.S. Pat. No. 4,517,373 and Japanese Patent Application J-60-130,548.

The appropriately substituted acids and acid halides of the formula (5) are commercially available or prepared from known starting materials utilizing standard chemical transformations.

The compounds of the formula (II) wherein Z is hydrogen or a pharmaceutically acceptable salt thereof are readily prepared by the mild basic hydrolysis of the lacetone moiety of the compounds of formula (I), careful acidification and formation of the appropriate salt utilizing standard procedures.

The compounds of the formula (II) wherein Z is $C_{1-5}$ alkyl or a substituted $C_{1-5}$ alkyl may be conveniently prepared by the procedures described in U.S. Pat. No. 4,342,767.

The compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg to 2000 mg (preferably 5 to 100 mg) which may be given in two to four divided doses. Higher doses may be favorably employed as required.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

The intrinsic HMG-CoA reductase inhibition activity of the claimed compounds is measured in the in vitro protocol published in *J. Med. Chem.*, 28, p. 347-358 (1985) and described below:

Isolation of HMG-CoA Reductase

Male Holtzman Sprague-Dawley rats (225-250 g) were kept on reversed lighting and fed Purina rat chow containing 3% cholestyramine for 7 days preceding their sacrifice by $CO_2$ asphyxiation. Livers were removed 6 hours into the dark cycle and used immediately to prepare microsomes. HMG-CoA reductase was solubilized from the freshly prepared microsome by the method of Heller and Shrewsbury [*J. Biol. Chem.*, 1976, 251, 3815[and purified through the second ammonium sulfate precipitation step as described by Kleinsek et al, [*Proc. Natl. Acad. Sci USA*, 1977, 74, 1431]. The enzyme preparation was tested for HMG-CoA reductase potency and diluted with 100 nM phosphate buffer (pH 7.2) so that 100 μl of the enzyme solution, when added to the assay control, gave a value of 50,000-60,000 dpm. The enzyme preparation was stored at $-80°$ C.

HMG-CoA Reductase Inhibition Assay

The assay is essentially the procedure of Shefer et al. [*J. Lipid Res.*, 1972, 13, 402]. The complete assay medium contained the following in a total volume of 0.8 ml: phosphate buffer, pH 7.2, 100 mM; $MgCl_2$, 3 mM; NADP, 3 nM; glucose 6-phosphate, 10 mM; glucose-6-phosphte dehydrogenase, 3 enzyme units; reduced glutathione, 50 mM; HMG-CoA (glutaryl-3-$^{14}$C, New England Nuclear), 0.2 mM (0.1 μCi); and partially purified enzyme stock solution, 100 μL.

Test compounds or compactin (after first being converted to the sodium salt of their dihydroxy acid form in situ by addition of 1N NaOH (1 equivalent) were added to the assay system in 10-μL volumes at multiconcentration levels. After a 40-minute incubation at 37° C. with shaking and exposure to air, the reaction was stopped by the addition of 0.4 mL of 8N HCl. After an additional 30-minute incubation at 37° C. to ensure the complete lactonization of mevalonic acid to mevalonolactone, 0.2 ml of the mixture was added to an 0.5 ×5.0 cm column containing 100–200 mesh BioRex 5, chloride form (Bio-Rad), wetted with distilled water, as described by Alberts et al., [*J. Proc. Natl. Acad. Sci. U.S.A.*, 1980, 77, 3957]. The unreacted 8 $^{14}$C]HMG-CoA was absorbed on the resin and the [$^{14}$C]mevalonolactone was eluted with distilled water (2×1ml) directly into 7-ml scintillation vials. Five milliliters of Aquasol-2 (New England Nuclear) was added to each vial, and radioactivity was measured in a Packard Tri Carb Prias scintillation counter. $IC_{50}$ value were determined by plotting percentage inhibition against test compound concentration and fitting a straight line to the resulting data by using the least-squares method. For estimation of relative inhibitory potencies, compactin was assigned a value of 100 and the $IC_{50}$ value of the test compound was compared with that of compactin determined simultaneously.

Representative of the intrinsic HMG-CoA reductase inhibitory activities of the claimed compounds, tabulated below for a number of the claimed compounds are the relative potencies for said compounds.

TABLE 1

| I | Relative Potency[1] |
|---|---|
| $\begin{array}{c}O\quad CH_3\\ \parallel\quad \mid\\ CH_3OCCH_2C-\\ \mid\\ CH_3\end{array}$ | 87 |
| $\begin{array}{c}O\quad CH_3\\ \parallel\quad \mid\\ CH_3OC-C-\\ \mid\\ CH_3\end{array}$ | 59 |

[1]Relative to compactin which was arbitrarily assigned a value of 100.

relative to compactin which was arbitrarily assigned a value of 100.

Included within the scope of this invention is the method of treating arteriosclerosis, familal hypercholesterolemia or hyperlipidemia which comprises administering to a subject in need of such treatment a nontoxic therapeutically effective amount of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims appended hereto.

EXAMPLE 1

Preparation of
6(R)-[2-[8(S)-(2,2-dimethyl-3-methoxy-3-oxopropionyloxy)-2(S),6(R)-dimethyl-1,2,6,7,8,8a(R)-hexahydronaphthyl-1(S)-]ethyl]-4(R)-hydroxy-3,4,5,6-tetrahydro-2H-pyran-2-one

(a) Methyl 2,2-diemthylmalonate (1a)

To a stirred solution of dimiethyl 2,2-dimethylmalonate (22.1 g, 138 mmol) in methanol (40 ml) at ambient temperature was added dropwise a solution of sodium hydroxide (5.52 g, 138 mmol) in water (20 ml). The reaction mixture was stirred for about 16 hours and then concentrated in vacuo at ambient temperature. The aqueous residue was cooled to 0°–5° C. and acidified with 6N hydrochloric acid. The aqueous mixture was saturated with sodium chloride and extracted with diethyl ether (2×150 ml). The combined extracts were washed with saturated aqueous sodium chloride (2×100 ml), dried over magnesium sulfate and concentrated in vacuo to give a colorless oil. The oil was purified by distillation at 15 mmHg to give the desired product which solidified on cooling. m.p. 35°–8° C.

NMR (CDCl$_3$) δ=1.50 (6H, s), 3.78 (3H, s).

(b) Methyl 2,2-dimethylmalonylchloride (1b)

To a stirred solution of the compound (1a) (5.0 g, 34.2 mmol) in dry benzene (25 ml) and dimethylformamide (2 drops) at ambient temperature was added oxalyl chloride (3.73 ml, 42.8 mmol). The reaction mixture was stirred for about 2 hours and the solvent removed in vacuo. The desired product was distilled at reduced pressure to yield a colorless liquid. b.p. 61°–2° C. at 15 mmHg.

NMR(CDCl$_3$) δ=1.56 (6H, s), 3.80 (3H, s).

(c) 6(R)-[2-[8(S)-(2,2-Dimethyl-3-methoxy-3-oxopropionyloxy)-2(S),6(R)-dimethyl-1,2,6,7,8,8a(R)-hexahydronaphthyl-1(S)]ethyl]-4(R)-(dimethyl-tert-butylsilyloxy)-3,4,5,6-tetrahydro-2H-pyran-2-one (1c)

To a stirred solution of 6(R)-[2-[8(S)-hydroxy-2(S),6(R)-dimethyl-1,2,6,7,8,8a(R)-hexahydronaphthyl-1(S)]ethyl]-4(R)-tert-butyldimethylsilyloxy-3,4,5,6tetrahydro-2H-pyran-2one (2.17 g, 5.0 mmol) in dry pyridine (25 ml) was added 4-pyrrolidinopyridine (148 mg, 1 mmol) and the reaction mixture under nitrogen was heated to 100° C. To the stirred reaction mixture at 100° C. was added the compound (1b) (1.64 g, 10 mmol). After 4 hours, additional compound (1b) (1.64 g, 10 mmol) was added. After 12 hours, the reaction mixture was allowed to cool to ambient temperature. The pyridine solvent was removed in vacuo and the residue suspended in diethyl ether (200 ml). The mixture was washed with water (50 ml) containing 3N hydrochloric acid (10 ml), saturated aqueous sodium bicarbonate (25 ml) and saturated aqueous sodium chloride (2×25 ml), dried over magnesium sulfate and concentrated in vacuo to give a viscous oil. The oil was chromatographed on a 5×15 cm column of silica gel eluted with 50 percent diethyl ether/hexane to afford the desired product and a minor amount of the compound (1a) as a semisolid. This was used in the next step without further purification.

(d) 6(R)-[2-[8(S)-(2,2-Dimethyl-3-methoxy-3-oxopropionyloxy)-2(S),6(R)-dimethyl-1,2,6,7,8,8a(R)-hexahydromaphthyl-1(S)]ethyl]-4(R)-hydroxy-3,4,5,6-tetrahydro-2H-pyran-2-one To a stirred solution of the compound (1c) (3.8 g, 6.75 mmol) in tetrahydrofuran (25 ml) was added acetic acid (1.2 g, 20 mmol) and tetra-n-butylammonium fluoride.3-H$_2$O (4.73 g, 15 mmol). The reaction mixture was heated to 60°–70° C. for 4 hours. The reaction mixture was then cooled to ambient temperature and poured into diethyl ether (200 ml). The mixture was washed with 1N hydrochloric acid (10 ml), saturated aqueous sodium bicarbonate (10 ml) and saturated aqueous sodium chloride (2×25 ml), dried over magnesium sulfate and concentrated in vacuo to a viscous oil. The oil was chromatographed on a 5×18 cm column of silica gel eluted with 15 percent acetone:methylene chloride to afford the product as a solid m.p. 94°–7° C. This material was rechromatographed on a 5×17 cm column of silica gel eluted with 20 percent isopropanol/hexane (1L) and 25 percent isopropanol/hexane to give the desired product, which after trituration in hexane was a white solid m.p. 103°–4° C.

Anal. Calc'd for $C_{25}H_{36}O_7$: C, 66.94; H, 8.09. Found: C, 67.10; H, 8.37.

NMR (CDCl$_3$) δ=0.88 (3H,d, J=7Hz), 1.06 (3H, d J=7 Hz), 1.42 (6H, s) 3.66 (3H, s), 4.38 (H, m), 4.55 (H, m), 5.42 (H, m), 5.49 (H, m), 5.78 (H, dd, J=10 Hz, 6 Hz), 5.96 (H, d, J=10 Hz)

EXAMPLE 2

Preparation of
6(R)-[2-[8(S)-(2,2-Dimethyl-3-methoxycarbonylpropionyloxy)-2(S),
6(R)-dimethyl-1,2,6,7,8,8a-(R)-hexahydronaphthyl-1(S)]ethyl]4(R)-hydroxy-3,4,5,6-tetrahydro-2H-pyran-2-one

(a) 4-Methyl 2,2-dimethylsuccinate (2a)

To a stirred solution of 2,2-dimethylsuccinic acid (25 g, 171 mmol) in methanol (125 ml) was added concentrated sulfuric acid (1 ml) and the reaction mixture was refluxed for 2 hours. The majority of the methanol was removed in vacuo and the residue treated with saturated aqueous sodium bicarbonate (100 ml). The mixture was extracted with diethyl ether (200 ml). The aqueous phase was acidified with 12N hydrochloric acid and then saturated with sodium chloride. This mixture was extracted with diethyl ether (3×100 ml). The combined extracts were washed with saturated aqueous sodium chloride (2 ×25 ml), dried over magnesium sulfate and concentrated in vacuo to give a colorless oil. The oil was distilled at reduced pressure to yeild the desired product. b.p. 112°–115° C. at 0.3 mmHg.

NMR(CDCl$_3$) δ=1.31 (6H, s ), 2.62 (2H, s), 3.65 (3H, s).

(b) 4-Methyl 2,2-dimethylsuccinyl chloride (2b)

To a stirred solution of the compound (2a)(4.8 g, 30 mmol) in benzene (20 ml) and oxalyl chloride (4.18 g, 33 mmol) was added dimethylformamide (1 drop) and the reaction mixture stirred for 1 hour at ambient temperture. To the reaction mixture was added dimethylformamide (1 drop) and the reaction mixture stirred for an additional 1 hour at ambient temperature. The solvent was removed in vacuo and the residue, distilled at reduced pressure to yeild the desired product as a pade yellow liquid. b.p. 96°-98° C. at 17 mmHg.

NMR(CDCl$_3$) δ=1.39 (6H, s), 2.74 (2H, s), 3.70 (3H, s).

(c)
6(R)-[2-[8(S)-(2,2-Dimethyl-3-methoxy-carbonylpropionyloxy)-2(S),6(R)-dimethyl-1,2,6,7,8,8a(R)-hexahydronaphthyl-1(S)]-ethyl]-4(R)-(dimethyl-tert-butylsilyloxy)-3,4,5,6-tetrahydro-2H-pyran-2-one (2c)

Utilizing the general procedure of Example 1(c), 6(R)-[2-[8(S)-hydroxy-2(S),6(R)-dimethyl-1,2,6,7,8,8a(R)-hexahydronaphthyl-1(S)]ethyl]-4(R)-(tert-butyldimethylsilyloxy)-3,4,5,6-tetrahydro-2H-pyran-2-one (1.08 g, 2.5 mmol) was reacted with the compound (2b) (0.89 g, 5.0 mmol) to give the desired product as a viscous pale yellow oil.

(d)
6(R)-[2-[8(S)-(2,2-Dimethyl-3-methoxy-carbonylpropionyloxy)-2(S),6(R)-dimethyl-1,2,6,7,8,8a(R)-hexahydronaphthyl-1(S)]-ethyl]-4(R)-hydroxy-3,4,5,6-tetrahydro-2H-pyran-2-one Utilizing the general procedure of Example 1(d), the compound (2c) (1.4 g, 2.42 mmol) was converted into the desired product.

Anal. Calc'd for C$_{26}$H$_{38}$O$_7$: C, 67.51; H, 8.28. Found C, 67.41; H 8.66.

NMR (CDCL$_3$) δ=0.91 (3H, d, J=7 Hz), 1.11 (3H, d, J=7 Hz), 1.28 (3H, s), 1.30 (3H, s), 3.65 (3H, s), 4.38 (H, m), 4.70 (H, m), 5.43 (H, m), 5.53 (H, m), 5.38 (H, dd, J=10 Hz, 6 Hz), 6.00 (H, d, J=10 Hz)

EXAMPLES 3–10

Utilizing the general procdures of Example 1 the following compounds are prepared from the appropriately substituted acid or acid chloride and compactin, mevinolin and the dihydro and tetrahydro analogs thereof.

TABLE 2

| Compound | T | T$_1$ | b | c | d |
|---|---|---|---|---|---|
| 3 | HOCCH$_2$—C(CH$_3$)(H)—, with C=O | CH$_3$ | db | — | db |
| 4 | C$_2$H$_5$OC—C(C$_2$H$_5$)(CH$_3$)—, with C=O | CH$_3$ | db | — | db |
| 5 | C$_3$H$_7$OCCH$_2$C(CH$_3$)—, with C=O | H | — | db | — |
| 6 | CH$_3$OCC—C(CH$_3$)(CH$_3$)—, with C=O and OCH$_3$ | H | — | — | — | db = double bond

TABLE 3

| Compound | T | T$_1$ | T$_2$ | T$_3$ | a | b | c | d |
|---|---|---|---|---|---|---|---|---|
| 7 | CH$_3$OCC—(CH$_3$)—, with C=O and OCH$_3$ | OH | H | H | — | db | — | db |
| 8 | CH$_3$OCCH$_2$C(CH$_3$)—, with C=O | OH | H | H | — | db | — | db |
| 9 | C$_2$H$_5$OC—C(CH$_3$)(H)—, with C=O | — | CH$_3$ | OH | db | — | db | — |

TABLE 3-continued

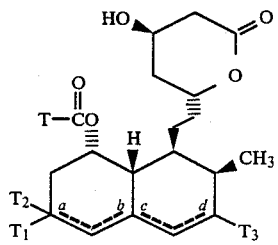

| Compound | T | $T_1$ | $T_2$ | $T_3$ | a | b | c | d |
|---|---|---|---|---|---|---|---|---|
| 10 | $HOOC-CH_2CH_2\underset{CH_3}{\overset{CH_3}{\underset{|}{\overset{|}{C}}}}-$ | $CH_3$ | OH | $CH_3$ | H | — | — | — | — |

EXAMPLE 11

Preparation of Alkali and Alkaline Earth Salts of Compound II

To a solution of the lactone from Example 1(d) (42 mg) in ethanol (2 ml) is added aqueous NaOH (1 equivalent). After one hour at room temperture, the mixture is taken to dryness in vacuo to yield the sodium salt of Compound II.

In like manner the potassium salt is prepared using one equivalent of potassium hydroxide, and the calcium salt using one equivalent of CaO.

EXAMPLE 12

Preparation of Methyl Ester of Compound II

To a solution of 400 mg of the lactone from Example 1(d) in 100 ml of absolute methanol is added 10 ml 0.1 M sodium methoxide in absolute methanol. This solution is allowed to stand at room temperture for one hour, is then diluted with water and extracted twice with ethyl acetate; the ethyl acetate, dried over anhydrous sodium sulfate, is removed in vacuo to yield the methyl ester of Compound II.

In like manner, by the use of equivalent amounts of propanol, butanol, isobutanol, t-butanol, amyl alcohol, isoamyl alcohol, 2-dimethylamino-ethanol, benzyl alcohol, phenethanol, 2-acetamidoethanol, and the like, the corresponding esters are obtained.

EXAMPLE 13

Preparation of free Hydroxy Acids

The sodium salt of the compound II from Example 11 is redissolved in 2 ml of ethanol-water (1:1) and added to 10 ml of 1N hydrochloric acid from which the hydroxy acid is extracted with ethyl acetate. The latter solvent is washed once with water, dried, and removed in vacuo with a bath temperature not exceeding 30° C. The hydroxy acid derived slowly reverts to the lactone on standing.

EXAMPLE 14

As a specific embodiment of a composition of this invention, 20 mg of the lactone from Example 1(d) is formulated with sufficient finely divided lactose to provide a total amount of 580 to 590 mg to fill a size 0 hard gelatin capsule.

What is claimed is:

1. A compound represented by the following general structural formula (II')

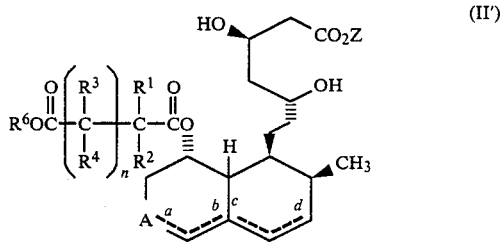

wherein:
n is 0 to 1;
$R^1$ is $C_{1-3}$alkyl;
$R^2$ is hydrogen or $C_{1-3}$alkyl;
$R^3$ is hydrogen or $C_{1-3}$alkyl;
$R^4$ is hydrogen or $C_{1-3}$alkyl;
$R^6$ is hydrogen or $C_{1-3}$alkyl;

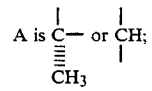

and
a, b, c and d represent single bonds, one of a, b, c or d represent a double bond, or both a and c or both b and d represent double bonds;
Z is hydrogen, $C_{1-5}$alkyl, or $C_{1-5}$alkyl substituted with a member of the group consisting of phenyl, dimethylamino or acetylamino; or a pharmaceutically acceptable salt of a compound of the formula ($II^{40}$) in which Z is hydrogen.

2. A compound according to Claim 1 wherein $R^3$ and $R^4$ are $C_{1-3}$alkyl; and a, b, c and d represent single bonds or both b and d represent double bonds.

3. A compound according to claim 1 wherein
$R^1$ is methyl;
$R^2$ is methyl; and
$R^3$ and $R^4$ are hydrogen.

4. A hypocholesterolemic, hypolipidemic pharmaceutical composition comprising a nontoxic therapeutically effective amount of a compound of claim 3 and a pharmaceutically acceptable carrier.

5. A composition according to claim 4 wherein $R^3$ and $R^4$ are $C_{1-3}$alkyl; and a, b, c and d represent single bonds or both b and d represent double bonds.

6. A composition according to claim 4 wherein
  $R^1$ is methyl;
  $R^2$ is methyl;
  $R^3$ and $R^4$ are hydrogen.

7. A method of inhibiting cholesterol biosynthesis comprising the administration to a subject in need of such treatment a nontoxic therapeutically effective amount of a compound of claim 1.

8. A method according to Claim 7 wherein $R^3$ and $R^4$ are $C_{1-3}$alkyl; and a, b, c and d represent single bonds or both b and d represent double bonds.

9. A method according to claim 7 wherein
  $R^1$ is methyl;
  $R^2$ is methyl;
  $R^3$ and $R^4$ are hydrogen.

10. A compound of Claim 3 which is 7-[1,2,6,7,8,8a(R)-hexahydro-2(S),6(R)-dimethyl-8(S)-(2,2-dimethyl-3-methoxy-3-oxopropionyloxy-1(S)-naphthyl]-3(R),5(R)-dihydryoxyheptanoic acid.

11. A compound of Claim 3 which is 7-[1,2,6,7,8,8a(R)-hexahydro-2(S),6(R)-dimethyl-8(S)-(2,2-dimethyl-3-methoxycarbonylpropionyloxy)-1(S)-naphthyl]-3(R),5(R)-dihydroxyheptanoic acid.

12. A composition according to claim 6 in which the therapeutically-active ingredient is selected from;
  7-[1,2,6,7,8,8a(R)-hexahydro-2(S),6(R)-dimethyl-8(S)-(2,2-dimethyl-3-methoxy-3-oxopropionyloxy)-1(S)-naphthyl]-3(R),5(R)-dihydroxyheptanoic acid, or
  7-[1,2,6,7,8,8a(R)-hexahydro-2(S),6(R)-dimethyl-8(S)-(2,2-dimethyl-3-methoxycarbonylpropionyloxy)-1(S)-naphthyl]-3(R),5(R)-dihydroxyheptanioc acid.

13. A method according to claim 7 in which the therapeutically-active ingredient is selected from:
  7-[1,2,6,7,8,8a(R)-hexahydro-2(S),6(R)-dimethyl-8(S)-(2,2-dimethyl-3-methoxy-3-oxopropionyloxy)-1(S)-naphthyl]-3(R),5(R)-dihydroxyheptanoic acid, or
  7-[1,2,6,7,8,8a(R)-hexahydro-2(S),6(R)-dimethyl-8(S)-(2,2-dimethyl-3-methoxycarbonylpropionyloxy)-1(S)-naphthyl]-3(R),5(R)-dihydroxyheptanoic acid.

* * * * *